US009561315B1

(12) United States Patent
Vincelli et al.

(10) Patent No.: US 9,561,315 B1
(45) Date of Patent: Feb. 7, 2017

(54) MINIATURIZED CARDIOPULMONARY BYPASS CIRCUIT FOR A MOUSE MODEL

(71) Applicants: Jay Vincelli, West Lebanon, NH (US); David McClatchy, Annapolis, MD (US); Stephanie Wolf, Madison, WI (US); Ryan J. Halter, Orford, NH (US)

(72) Inventors: Jay Vincelli, West Lebanon, NH (US); David McClatchy, Annapolis, MD (US); Stephanie Wolf, Madison, WI (US); Ryan J. Halter, Orford, NH (US); James Yun, Lebanon, NH (US)

( * ) Notice: Subject to any disclaimer, the term of this patent is extended or adjusted under 35 U.S.C. 154(b) by 125 days.

(21) Appl. No.: 14/184,273

(22) Filed: Feb. 19, 2014

Related U.S. Application Data

(60) Provisional application No. 61/766,153, filed on Feb. 19, 2013.

(51) Int. Cl.
*A61M 1/00* (2006.01)
*A61M 1/14* (2006.01)

(52) U.S. Cl.
CPC .......... *A61M 1/14* (2013.01); *A61M 2250/00* (2013.01)

(58) Field of Classification Search
CPC ........ A61M 1/3627; A61M 1/34; A61M 1/16; A61M 1/3639; A61M 1/3621; A61M 1/3666; A61M 1/1998; A61M 1/169; A61M 2025/10528; A61M 2250/00
USPC ............................ 604/4.01–6.16; 422/44–46
See application file for complete search history.

(56) References Cited

U.S. PATENT DOCUMENTS

| | | | | |
|---|---|---|---|---|
| 3,881,483 A * | 5/1975 | Sausse | ............... | A61M 1/3621 210/110 |
| 4,749,551 A * | 6/1988 | Borgione | ............ | A61M 1/1698 128/DIG. 3 |
| 5,064,358 A * | 11/1991 | Calari | ................ | F04B 43/1292 417/475 |
| 6,682,698 B2 * | 1/2004 | Chambers | ........... | A61M 1/1678 422/44 |

* cited by examiner

*Primary Examiner* — Philip R Wiest
(74) *Attorney, Agent, or Firm* — Loginov & Associates, PLLC; William A. Loginov

(57) ABSTRACT

A miniaturized cardiopulmonary bypass circuit for a mouse comprises at least one venous catheter connected to a patient, a dual channel peristaltic pump having one channel to move the blood by tubing from the patient, an oxygenator that removes gases from the blood and mixes the blood with fresh gases to oxygenate the blood, the blood being moved from the oxygenator to the arterial catheter by the dual channel peristaltic pump, and an arterial catheter. The blood is pumped by a two-channel roller pump into an inlet nozzle, where the flow of blood is transformed from tubular flow to planar flow. Gas exchange occurs inside the case while the blood flows down the central component. Blood then flows down the central component into the arterial reservoir. The arterial reservoir is connected to the second channel of the pump, and returned to the patient through a cannula.

13 Claims, 7 Drawing Sheets

MINIATURIZED CARDIOPULMONARY BYPASS CIRCUIT FOR A MOUSE MODEL

RELATED APPLICATION

This invention relates to cardiopulmonary bypass devices and more particularly to such devices employed in cardiopulmonary bypass surgery for small mammals.

FIELD OF THE INVENTION

This application claims the benefit of U.S. Provisional Application Ser. No. 61/766,153, filed Feb. 19, 2013, entitled MINIATURIZED CARDIOPULMONARY BYPASS CIRCUIT FOR A MOUSE MODEL, by Jay Vincelli, et al., the entire disclosure of which is herein incorporated by reference.

BACKGROUND OF THE INVENTION

Prior to 1951, whenever surgeons needed to perform cardiac surgery, the only option was for them to operate on the beating heart as it continued to pump blood. On Apr. 5, 1951, Dr. Clarence Dennis conducted the first temporary takeover of both the heart and lung functions. Unfortunately, the patient did not survive due to a congenital heart defect. However, this stirred the interest of other doctors throughout the world, and soon after Dr. John Gibbon Jr. completed the first successful human heart surgery in 1953.

Now, over fifty years later, cardiopulmonary bypass (CPB) surgery is routinely done for patients that require cardiac surgery. Even though general surgical complications from cardiopulmonary bypass aren't frequent, when they occur, these complications are associated with a high mortality. A study was done at the University of Virginia Health Sciences Center in which 1831 patients had undergone CPB for a three-year period. There were 39 general surgical complications defined (incidence of ~2.0%) and there were 14 deaths—a mortality of 38.9% out of the patients with surgical complications.

Unfortunately, there are limited resources available to investigate side effects of CPB on certain populations. These populations include the elderly, those with specific genetic dispositions, such as diabetes, and patients with other illnesses. Furthermore, human CPB demographics are changing. There are currently more patients with genetic predispositions and patients who are getting older and sick. More patients have other health issues as well. There needs to be a miniaturized model to study these impacts on a cellular and molecular level. Mice represent the perfect study model because they are inexpensive, can be inbred, genetically altered and have a similar anatomy to that of humans.

Designs in the prior art include thin film centrifugal oxygenators, membrane oxygenators, and a bubble oxygenator. The bubble oxygenator has been shown to be effective in bypass circuits for small animal models, but it requires a large reservoir of blood and cannot be sufficiently miniaturized. Similarly, the membrane oxygenator has also been shown to be effective in small animal bypass circuits for rats, but produces a prime volume an order of magnitude greater than is needed for mouse testing. However, the length of tubing, and therefore prime volume, needed to oxygenate the blood can be excessive for mouse testing. The thin film centrifugal oxygenator has been shown to be effective and it also has a relatively low prime volume, but the spinning disk and associated moving components are at risk for failing. Furthermore, the uncontrolled nature of hurling blood from a spinning disk necessitates an unsuitably large prime volume to ensure the reservoir stays filled to prevent gas emboli.

It is therefore desirable to provide a device with a sufficiently small prime volume suitable for use in performing cardiopulmonary surgery on mice and other small mammals.

SUMMARY OF THE INVENTION

This invention overcomes the disadvantages of the prior art by providing a novel, thin film-type oxygenator, that is generally free of moving parts, and defines the smallest prime volume of any known device and is therefore substantially effective for use in experimental cardiopulmonary surgeries related to mice and other small mammals.

Cardiopulmonary Bypass is routinely performed for cardiac surgery with great success; however, when complications do arise they are associated with high mortality. Furthermore, the demographics for patients who are put on CPB are expanding to include the elderly, diabetics, and people with other genetic dispositions, but unfortunately there are very limited resources to study the effects of CPB on these populations. Transgenic mice that can have these dispositions pose as an advantageous area for CPB research, but mouse size CPB circuits are not yet fully developed. Currently, rat CPB circuits are most commonly used, but miniaturizing these circuits for mice require reducing the prime volume and flow rate by an order of magnitude while maintaining similar levels of oxygenation.

The main components of the circuit include the pump, oxygenator, and cannulas. For the prototype, a two-channel Clark Boxer 6000 Series peristaltic pump was used, which utilizes the two channels for the arterial and venous lines. The oxygenator's case was 3D printed out of ABS plastic. The inlet nozzle, central component, and arterial reservoir, were 3D printed out of Objet's MED610 biocompatible material.

The key concepts include blood being pumped by a two-channel roller pump and into an inlet nozzle, where the flow of blood is smoothly transformed from tubular flow to planar flow, creating a thin film around a narrow cylinder. Gas exchange occurs inside the case while the blood flows down the central component. A thin film of blood then flows down the central component into the arterial reservoir. The arterial reservoir is connected to the second channel of the pump, such that it is pumped at the same rate on both sides of the pump and maintains a constant flow rate, and returned to the patient through a cannula.

In an illustrative embodiment, a miniaturized cardiopulmonary bypass circuit for a mouse is comprised of at least one venous catheter connected to a patient for the removal of blood from the patient, a dual-channel peristaltic pump having one channel to move the blood by tubing from the patient, an oxygenator that removes gases from the blood and mixes the blood with fresh gases to oxygenate the blood, the blood being moved from the oxygenator to the arterial catheter by the dual channel peristaltic pump, and an arterial catheter. The oxygenator is comprised of an outer case, a blood inlet and outlet nozzle, a gas inlet and outlet nozzle, a central compartment, a central component, an arterial reservoir, tubing and barb fittings for gas connection. The gas inlet nozzle is located near the bottom of the outer case to generate a flow of gas that runs counter-current to the flow of blood to increase gas exchange. The central component is nested inside the nozzle to provide a smooth transition from tubular flow to planar flow.

BRIEF DESCRIPTION OF THE DRAWINGS

The invention description below refers to the accompanying drawings, of which.

DETAILED DESCRIPTION

Figure 1:
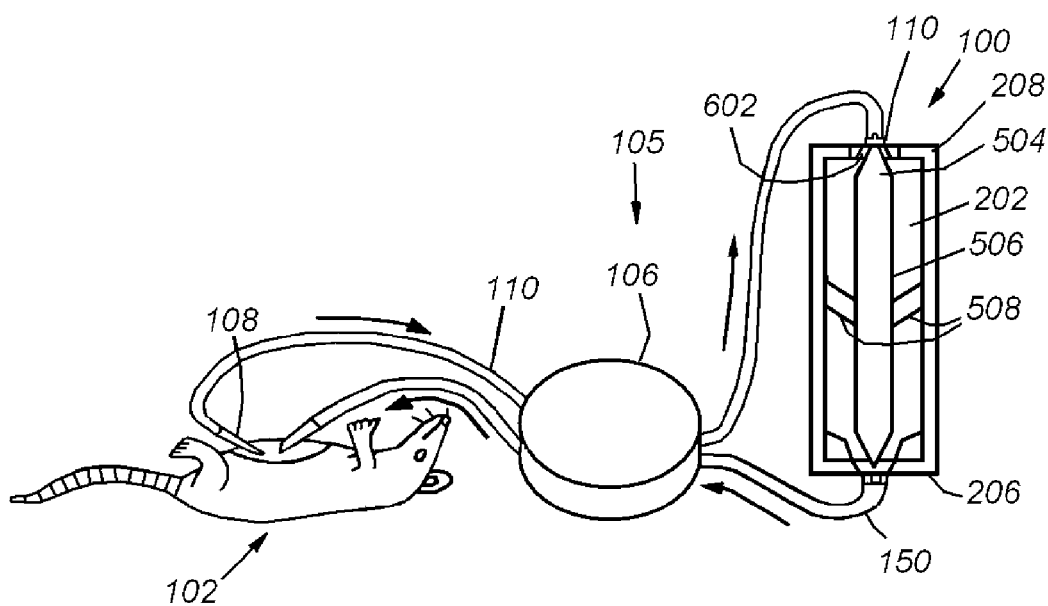
FIG. 1 is a perspective view of the overall circuit, according to an illustrative embodiment.

FIG. 1 is a perspective view of the overall circuit, including the patient 102, tubing 104, pump 106, and oxygenator 100, according to an embodiment. The patient's blood exits through at least one catheter cannula 108 and enters the CPB (cardiopulmonary bypass) circuit 105. A tube 110 that goes around one half of a two-channel roller peristaltic pump 106, connects the cannula 108 to the inlet nozzle 110 of the oxygenator 100. The conical, upper tip 504 of the central component 202 is in close proximity to the conical hole 602, such that the flow of blood smoothly transforms from tubular flow to planar flow around the central component 202. The blood then flows down the cylindrical, main body 506 of the central component 202. The small diameter of the main body 506 and surface tension causes a thin film of blood to develop as it flows downward with the aid of gravity. For gas exchange, gas flows counter-current to the flow of blood through a gas inlet port 302 (not shown herein, but explained more fully below) in the lower half of the case 206 and a gas outlet port 402 in the upper half of the case 208. The oxygenated blood then flows to the arterial reservoir 204 located in the lower half of the case 206 (not shown herein, but explained more fully below). A tube, connected to the second channel of the roller pump 207, connects the arterial reservoir 204 (not shown herein but described more fully below) to the return cannula 150 and back into the patient 102 at the same rate it is pumped into the oxygenator 100.

The pump can be a commercially available peristaltic pump, for example, a two-channel Clark Boxer 6000 Series peristaltic pump that utilizes the two channels for the arterial and venous lines. Other pumping mechanisms can be used, for example, two single-channel pumps dedicated to separate pumping of arterial and venous blood. The oxygenator's case can be 3D printed out of ABS plastic. The inlet nozzle, central component, and arterial reservoir, can be 3D printed out of Objet's MED610 biocompatible material. Other materials and production processes can be used, for example, casting.

Figure 2:
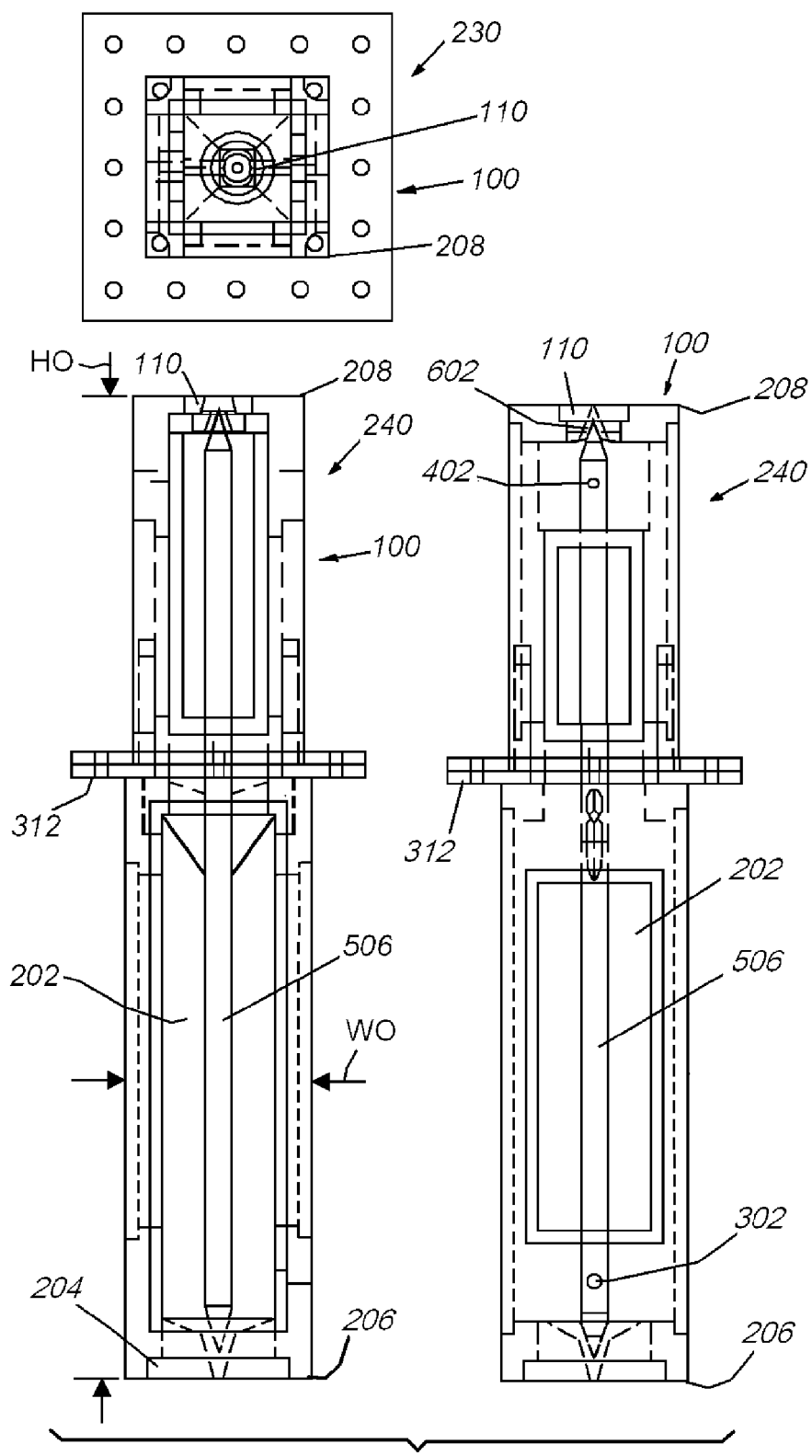
FIG. 2 is a view of the top, front and side of an oxygenator, according the illustrative embodiment.

FIG. 2 depicts the oxygenator 100 in its assembled configuration (without fasteners), showing a top view 230, a front view 240 and a side view 250. The oxygenator 100 requires a prime volume of 4.5 mL. This is an order of magnitude smaller than any known device and is appropriate for use in mouse testing. The overall height HO of the oxygenator 100 is approximately 275 mm. The overall width WO of the oxygenator 100 is approximately 86 mm. The empty weight (e.g., without fluid) of the oxygenator 100 is approximately 280 grams. All of the internal parts and fittings as described herein are appropriately sized and proportionate for the approximately stated dimensions. Such sizes can vary as appropriate to the application of the oxygenator (i.e. larger or smaller animals).

Figure 3:
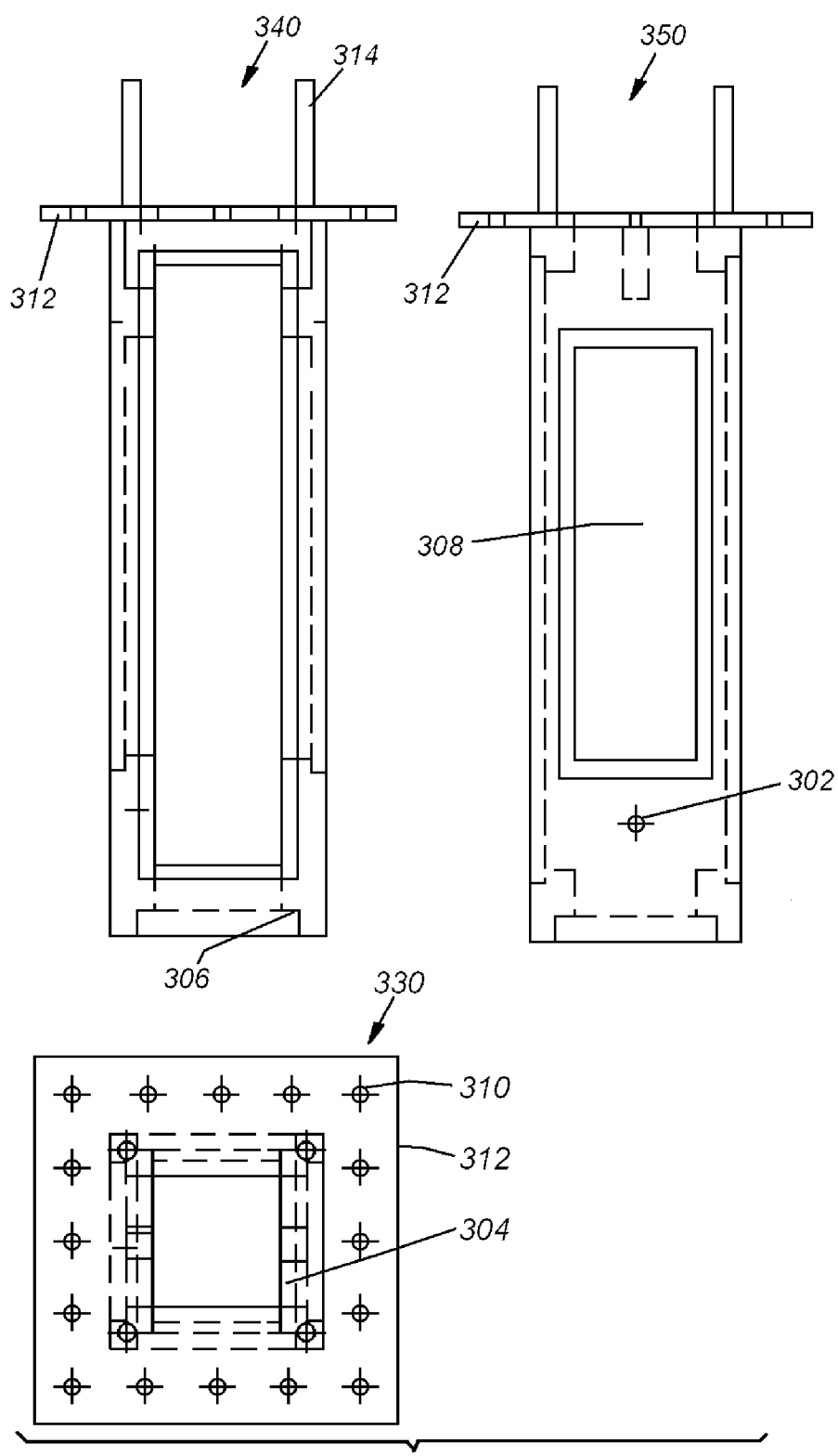
FIG. 3 is a view of the top, front and side of the lower half of the oxygenator, according to the illustrative embodiment.

FIG. 3 depicts lower half 206 of the oxygenator 100, showing a top view 330, a front view 340 and a side view 350. A port 302 located proximal to the arterial reservoir 204 is used for the gas inlet. Slots 304 are used to guide the central component 202 into the lower case 206 and prevents damage to the lower tip 502 of the central component 202, securing it into place with a press fit. The arterial reservoir slot 306 is used to secure the arterial reservoir 204 in place with a press fit. Windows 308 help verify that the central component is installed properly and to monitor the invention during operation and to allow for ready and straightforward viewing of the flow of blood at the inlet, around the central component, and at the arterial reservoir. The gas inlet nozzle is located near the bottom of the case to generate a flow of gas that runs counter-current to the flow of blood to increase gas exchange.

To help guide the upper half of the case 208 to the lower half of the case 206 during assembly, guide posts 314 are used, that have a smaller diameter than the guide post holes 402 in the upper case 208. The fastener holes 310 are used to secure the top half of the case 208 to the lower half of the case 206, although alternative methods of fastening can be used. The lower half of the case 206 can be cast, machined or 3D printed in materials capable of having tolerances necessary for the press fit surfaces.

Figure 4:
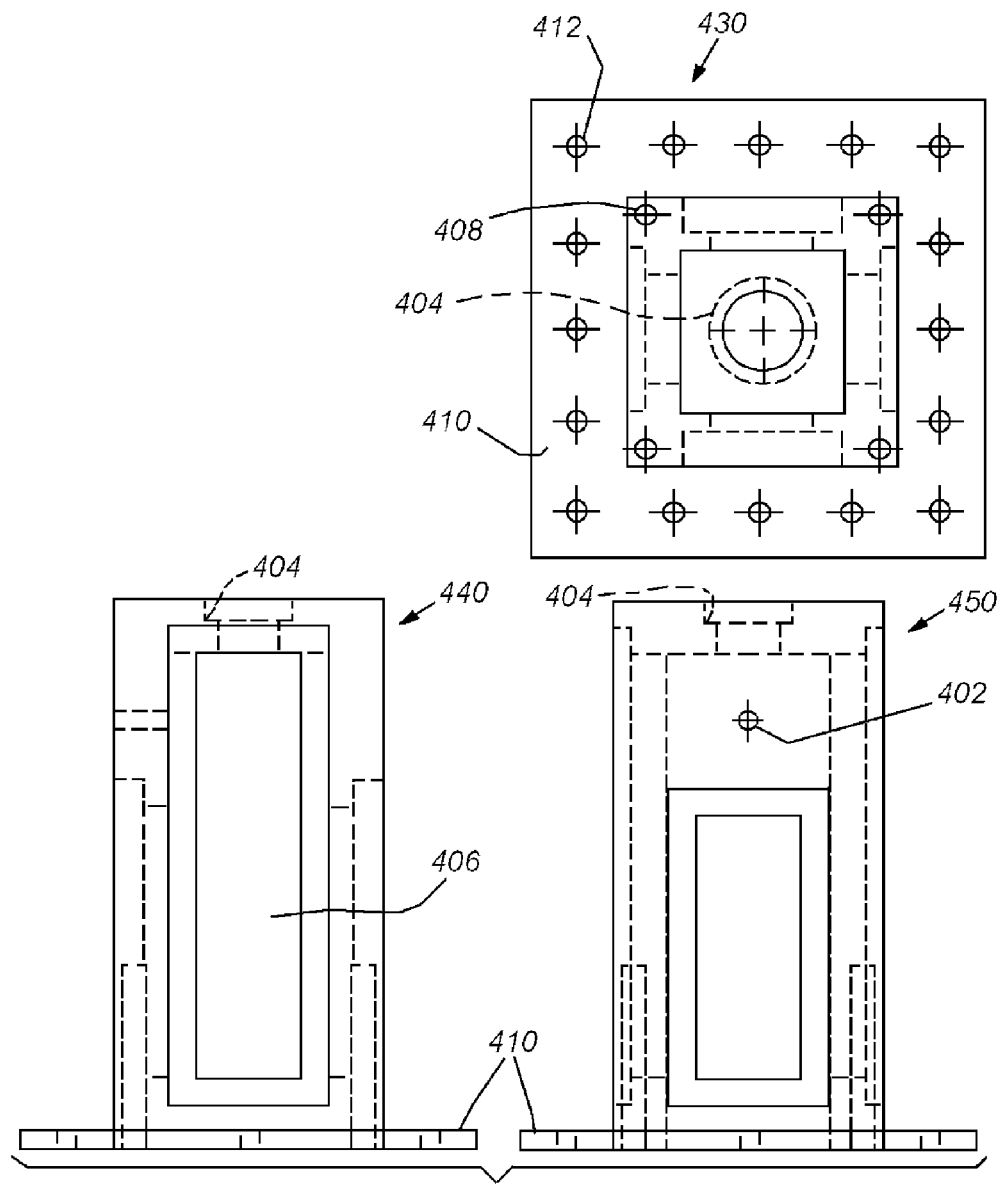
FIG. 4 is a view of the top, front and side of the upper half of the oxygenator, according to the illustrative embodiment.

FIG. 4 depicts the upper half of the oxygenator case 208, showing a top view 430, a front view 440 and a side view 450. Similar to the lower half of the case 206, a port 402, located proximal to the blood inlet nozzle 210 is used as the gas outlet. This orientation of gas inlet/outlet improves oxygenation performance by having the gas flowing counter current to the blood. The blood inlet nozzle slot 404 is used as a press fit surface to secure the blood inlet nozzle 210 in place. Windows 406 are used to monitor the performance of the invention during assembly and use. Guidepost holes 408 are used to guide the flange 410 of the upper half of the case 208 to the flange 313 of the lower half of the case 206, thereby preventing damage to the upper tip 504 of the central component 202 during assembly. Fastener holes 412 are used to secure the upper half of the case 208 to the lower half of the case 206. The upper half of the case 208 can be cast, machined or 3D printed in materials capable of having tolerances necessary for the press fit surfaces. The geometry of the slots where the central component is seated is constructed and arranged so that, during assembly, the arms of the central component can engage the slots and create a gap between the bottom tip of the central component and the arterial reservoir, preventing damage. Similarly, guide posts were designed to guide the top half of the case into the bottom half of the case to protect the upper tip of the central component. The nozzle diameter is constructed and arranged to ensure a low-enough blood velocity such that splattering will not occur. A barbed reducer is attached (for example by adhesive, welding, or press/snap fit) to the top of the inlet nozzle to provide a smooth transition between diameters and to connect tubing.

Figure 5:
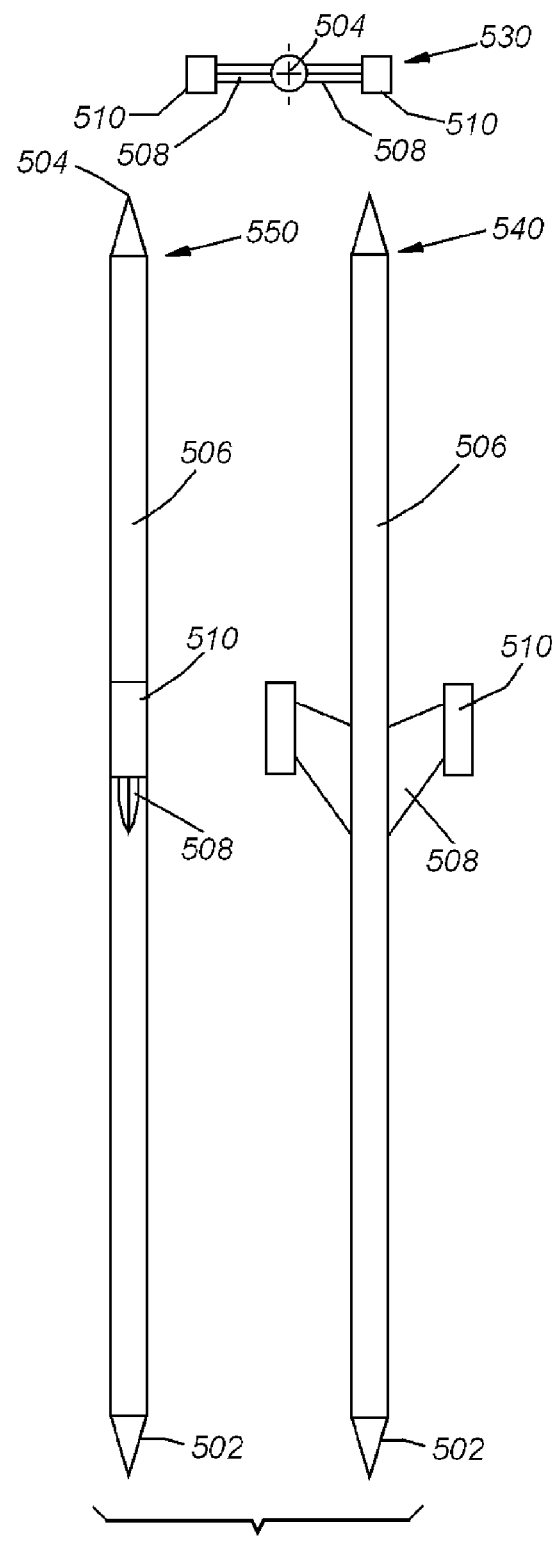
FIG. 5 is a view of the top, front and side of the central component of the oxygenator, showing the primary surface where gas exchange of the blood occurs, according to the illustrative embodiment.

FIG. 5 depicts the central component 202 of the oxygenator, showing a top view 530, a front view 540 and a side view 550. The main body 506 is cylindrical to ensure an even thickness blood film flowing across its surface, maximizing gas exchange. The upper tip 502 and lower tip 504 are conical in shape, that is used to transfer the flow of blood from tubular to planar across its surface at the inlet nozzle 210 and the arterial reservoir 204. Blocks 510 are located at the end of the arms 508, that are press fit into the lower half of the case 206 to secure the central component 202 within the oxygenator. This component can be cast, machined or 3D printed in materials capable of having tolerances necessary for the press fit surfaces. It can be constructed from a biocompatible material.

Figure 6:
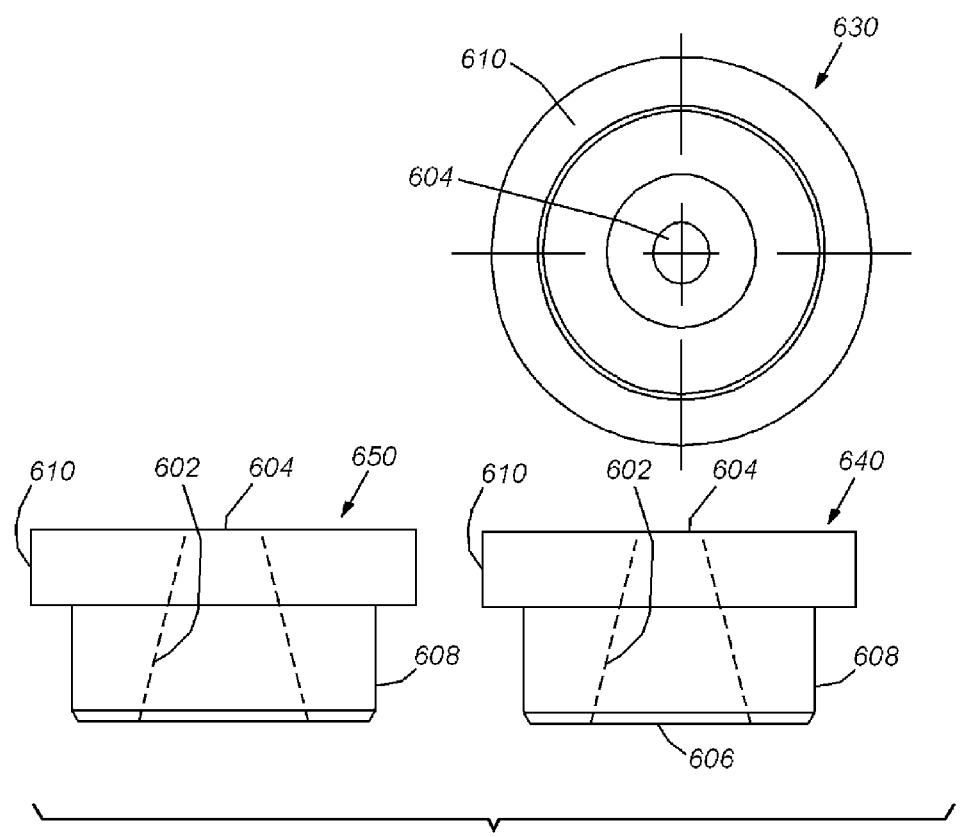
FIG. 6 is a view of the top, front and side of the inlet nozzle component, located on the upper case of the oxygenator, according to the illustrative embodiment.

FIG. 6 depicts the blood inlet nozzle 210 that is located in the inlet nozzle slot 404 of the upper half of the case 208, showing a top view 630, a front view 640 and a side view 650. A conical hole 602 is located along the central axis. Blood flows through a tube and into the top 606 of the conical hole 602 and is transferred into planar flow on the central component 202. Surface 608 is in a press fit with the upper half of the case 208 to secure it into place. The inlet nozzle 210 is fully seated in the upper half of the case 208 when the flange 610 makes contact with the upper half of the case 208. This component can be cast, machined or 3D printed in materials capable of having tolerances necessary for the press fit surfaces. The components are fabricated on all parts herein from a natural and/or synthetic biocompatible material, or a combination thereof (e.g., a rigid polymer and/or a metal).

Figure 7:
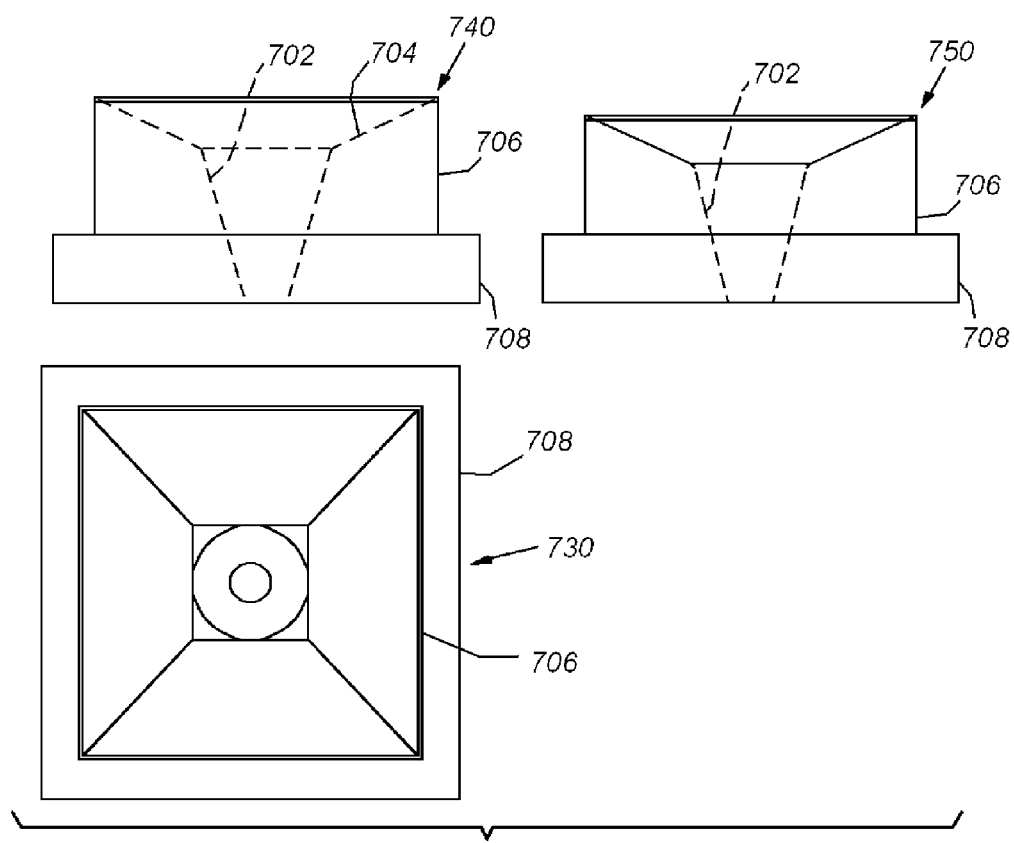
FIG. 7 is a view of the top, front and side of the arterial reservoir component, according to the illustrative embodiment.

FIG. 7 depicts the arterial reservoir 204 that is located on the lower half of the case 206, showing a top view 730, a front view 740 and a side view 750. A conical hole 702 is used to transfer the planar flow of blood on the central component 202 into tubular flow. In the case that blood accumulates at this component, a reservoir is used to contain the blood. Surface 706 is in a press fit with the lower half of the case 206 to secure it into place. The arterial reservoir 704 is fully seated when the flange 708 makes contact with the lower half of the case 206. This component can be cast, machined or 3D printed in materials capable of having tolerances necessary for the press fit surfaces.

It should be clear that the above-described oxygenator provides a highly effective, straightforward-to-use and significantly small-scale device for use in cardiopulmonary bypass surgery on mice and other small mammals. The absence of moving parts increases reliability and decreases construction costs.

The foregoing has been a detailed description of illustrative embodiments of the invention. Various modifications and additions can be made without departing from the spirit and scope if this invention. Each of the various embodiments described above can be combined with other described embodiments in order to provide multiple features. Furthermore, while the foregoing describes a number of separate embodiments of the apparatus and method of the present invention, what has been described herein is merely illustrative of the application of the principles of the present invention. For example, additional ports can be added to the lower half of the case 206 or the upper half of the case 208 for drug delivery. A control system can be attached or included with the lower half of the case 206 or the arterial reservoir 204 for adjusting the flow rate through the pump, if an alternative pump technology is used. While windows were included in the above description, they are not required for proper functioning of the oxygenator. This technology can be scaled up for higher blood flow rates, either by increasing the length and/or diameter of the central component and tubing, or by using several oxygenators in parallel, thereby allowing it to be adapted for use in larger animals and/or humans. Accordingly, this description is meant to be taken only by way of example, and not to otherwise limit the scope of this invention.

What is claimed is:

1. A system for a miniaturized cardiopulmonary bypass circuit for a mouse comprising:
    at least one venous catheter configured to be connected to the mouse for the removal of blood from the mouse;
    an oxygenator comprising a hollow outer case, a blood inlet nozzle, an arterial blood reservoir, an impermeable central rod within the hollow outer case, wherein blood flows over an exterior surface of the impermeable central rod as a film of flowing blood, and a gas inlet nozzle, wherein gas flows from the gas inlet nozzle into the hollow outer case forming a direct gas/blood interface with the film of flowing blood free of any membrane;
    at least one arterial catheter for the infusion of fresh blood from the oxygenator into an artery of the mouse; and
    a dual channel peristaltic pump to generate a flow of blood, the dual channel peristaltic pump having a first channel to move the blood by tubing from the from the venous catheter to the oxygenator, and the peristaltic pump having a second channel to transport the oxygenated blood to the arterial catheter.

2. The system as set forth in claim 1 wherein the outer case is split into two pieces for the installation of the impermeable central rod, inlet nozzle and arterial blood reservoir.

3. The system as set forth in claim 1 wherein the gas inlet nozzle is located adjacent to a bottom of the outer case to generate a flow of gas that runs counter-current to the flow of blood to increase gas exchange across the gas/blood interface.

4. The system as set forth in claim 1 wherein the impermeable central rod is nested inside the blood inlet nozzle to provide a smooth transition from a tubular flow of the blood to a planar flow of the blood as a film over an exterior surface of the impermeable central rod.

5. An oxygenator for cardiopulmonary bypass surgery comprising:
    a hollow outer case;
    a blood inlet nozzle;
    an arterial blood reservoir;
    an impermeable central rod within the hollow outer case, wherein blood flows over an exterior surface of the impermeable central rod as a film of flowing blood; and
    a gas inlet nozzle, wherein gas flows from the gas inlet nozzle into the hollow outer case forming a direct gas/blood interface with the film of flowing blood free of any membrane.

6. The oxygenator as set forth in claim 5 wherein the outer case is split into two pieces for the installation of the impermeable central rod, inlet nozzle and arterial blood reservoir.

7. The oxygenator as set forth in claim 6 wherein the gas inlet nozzle is located adjacent to a bottom of the outer case to generate a flow of gas that runs counter-current to the flow of blood to increase gas exchange.

8. The oxygenator as set forth in claim 6 wherein the impermeable central rod is nested inside the gas inlet nozzle to provide a smooth transition from a tubular flow of the blood to planar flow of the blood as a film over an exterior surface of the central rod.

9. The system as set forth in claim 1, wherein the blood flows freely through the oxygenator free of any pumping force.

10. The system as set forth in claim 2, the impermeable central rod being disposable and replaceable.

11. The oxygenator as set forth in claim 5, wherein the blood flows freely over the exterior surface of the impermeable central rod free of any pumping force.

12. The oxygenator as set forth in claim 6, wherein the impermeable central rod is disposable and replaceable.

13. A method of oxygenating blood comprising:
- guiding blood into a planar flow within the oxygenator of claim 5;
- allowing gravity to pull the planar flow of blood through the oxygenator free of any pumping force;
- pumping a gas through the oxygenator to form a gas/blood interface, the gas comprising at least oxygen, thereby oxygenating the blood.

\* \* \* \* \*